(12) United States Patent
Lintereur et al.

(10) Patent No.: US 11,944,785 B2
(45) Date of Patent: Apr. 2, 2024

(54) HEALTHCARE SERVICE MANAGEMENT VIA REMOTE MONITORING AND PATIENT MODELING

(71) Applicant: Medtronic MiniMed, Inc., Northridge, CA (US)

(72) Inventors: Louis J. Lintereur, Boise, ID (US); Catherine Tan Fogel, Porter Ranch, CA (US); Patrick E. Weydt, Moorpark, CA (US); Benyamin Grosman, Winnetka, CA (US); Mahta Sadeghzadeh, Los Angeles, CA (US)

(73) Assignee: Medtronic MiniMed, Inc., Northridge (CA)

( * ) Notice: Subject to any disclaimer, the term of this patent is extended or adjusted under 35 U.S.C. 154(b) by 685 days.

(21) Appl. No.: 17/112,321

(22) Filed: Dec. 4, 2020

(65) Prior Publication Data

US 2022/0176039 A1    Jun. 9, 2022

(51) Int. Cl.
| | |
|---|---|
| *A61M 5/172* | (2006.01) |
| *G06Q 30/04* | (2012.01) |
| *G16H 10/20* | (2018.01) |
| *G16H 20/17* | (2018.01) |
| *G16H 40/20* | (2018.01) |
| *G16H 40/40* | (2018.01) |

(Continued)

(52) U.S. Cl.
CPC ........... *A61M 5/1723* (2013.01); *G06Q 30/04* (2013.01); *G16H 10/20* (2018.01); *G16H 20/17* (2018.01); *G16H 40/20* (2018.01); *G16H 40/40* (2018.01); *G16H 40/67* (2018.01); *G16H 50/20* (2018.01); *G16H 50/30* (2018.01); *G16H 50/50* (2018.01); *G16H 50/70* (2018.01); *A61M 2205/3553* (2013.01); *A61M 2205/502* (2013.01); *A61M 2205/52* (2013.01); *A61M 2205/581* (2013.01); *A61M 2205/582* (2013.01); *A61M 2205/8206* (2013.01); *A61M 2230/201* (2013.01)

(58) Field of Classification Search
None
See application file for complete search history.

(56) References Cited

U.S. PATENT DOCUMENTS

| | | |
|---|---|---|
| 2007/0118399 A1 | 5/2007 | Avinash et al. |
| 2017/0235915 A1 | 8/2017 | Mansi et al. |

(Continued)

*Primary Examiner* — Manuel A Mendez
(74) *Attorney, Agent, or Firm* — Weaver Austin Villeneuve & Sampson LLP

(57) ABSTRACT

Devices, systems, and techniques for therapy delivery and healthcare management is described. In one example, a system comprises a delivery device configured to execute therapy information comprising a treatment schedule specifying one or more treatments over a time period, wherein for each of the one or more treatments, the therapy information comprises a treatment type and a treatment amount; and processing circuitry configured to: determine a modification to the therapy information based on a recommendation of a digital twin, wherein the digital twin determines an estimated glucose level expected to be within a healthy range if the delivery device executes the modification to therapy information; and in response to physician review of the modification to the therapy information, output, to a healthcare provider system for the patient, data indicating completion of a healthcare service corresponding to the physician review.

20 Claims, 7 Drawing Sheets

(51) Int. Cl.
  *G16H 40/67* (2018.01)
  *G16H 50/20* (2018.01)
  *G16H 50/30* (2018.01)
  *G16H 50/50* (2018.01)
  *G16H 50/70* (2018.01)

(56) References Cited

U.S. PATENT DOCUMENTS

| | | |
|---|---|---|
| 2017/0262605 A1 | 9/2017 | Wadhwa et al. |
| 2018/0358114 A1 | 12/2018 | Schecter |
| 2019/0005200 A1* | 1/2019 | Zimmerman .......... G16H 50/30 |
| 2019/0385728 A1 | 12/2019 | Bowland et al. |
| 2020/0185107 A1 | 6/2020 | Cox et al. |
| 2020/0203020 A1 | 6/2020 | Cox et al. |

* cited by examiner

HEALTHCARE SERVICE MANAGEMENT VIA REMOTE MONITORING AND PATIENT MODELING

TECHNICAL FIELD

The disclosure relates to medical systems and, more particularly, to medical systems for therapy for diabetes.

BACKGROUND

A patient with diabetes receives insulin from a pump or injection device to control the glucose level in his or her bloodstream. Naturally produced insulin may not control the glucose level in the bloodstream of a diabetes patient due to insufficient production of insulin and/or due to insulin resistance. To control the glucose level, a patient's therapy routine may include dosages of basal insulin and bolus insulin. Basal insulin, also called background insulin, tends to keep blood glucose levels at consistent levels during periods of fasting and is a long acting or intermediate acting insulin. Bolus insulin may be taken specifically at or near mealtimes or other times where there may be a relatively fast change in glucose level, and may therefore serve as a short acting or rapid acting form of insulin dosage.

SUMMARY

Devices, systems, and techniques for managing a glucose level in a patient are described. Physicians in general provide their patients with various healthcare services and through a healthcare provider (HCP), these healthcare services are logged and evaluated for different purposes (e.g., billing). HCPs, on behalf of the patients, handle the negotiation, billing, and payment for these healthcare services. To recoup costs for healthcare services rendered by any physician, that physician provides at least some evidence of the performance of each healthcare service. As explained in further detail herein, some physicians either are unable to or find it difficult to track patient services for the HCP to adequately be compensated (e.g., reimbursement). Some devices, systems, and techniques described herein eliminate that inability or difficulty by automatically communicating, to the HCP's system of computing devices, data indicating completion of the healthcare service or an event corresponding to the patient's response to the performance of the healthcare service.

As one example, one or more processors may execute a digital twin of the patient, where a digital twin is a digital replica of the patient and predicts how the patient will react to changes in therapy. In some examples, the digital twin may receive patient data, and the digital twin may simulate therapy information (e.g., device settings, treatment parameters, injection instructions) to determine more optimal therapy information based on the patient data. For instance, if the patient data indicates that the current therapy information result in glucose level of the patient being greater than desired, the digital twin may simulate how the patient will be affected by different therapy information to determine more optimal therapy information. A physician may then review the therapy information. The evaluating of patient data and generation of therapy information for physician review may be examples of items of proof used for invoicing, and the example techniques provide for a way in which to streamline generation of such proof.

Some devices, systems, and techniques may determine, based on the patient's digital twin, an estimated glucose level if the patient continues receiving treatment(s) under the current diabetes therapy. If that estimated glucose level is determined to be unhealthy, some devices, systems, and techniques described herein, based on the physician's input, may update the patient's diabetes therapy to include a new or different treatment. For example, the new or different treatment, as selected by the digital twin, will improve the patient's diabetes condition (e.g., causing the patient's glucose level to be within a healthy range). Some devices, systems, and techniques described herein output an invoice regarding that update for the HCP to acknowledge as a completed healthcare service and forward for reimbursement to whichever entity is ultimately paying for the completed healthcare service. Instead of requiring time-consuming research to identify the necessary information to be incorporated into that invoice, some devices, systems, and techniques described herein automatically generate the invoice, populate that information into the invoice, and communicate the invoice for the above-mentioned update as part of an evidentiary submission to the HCP of the completed healthcare service.

Hence, the present disclosure is directed to at least one improvement in a technical field of healthcare service management. In the present disclosure, the above-mentioned devices, systems, and techniques are described as practical applications of that improvement; for example, by employing remote monitoring/delivery services and patient modeling technologies, some devices, systems, and techniques described herein may control the patient's therapy delivery in such a manner that a delivery device administers the physician's treatment(s) to maintain a healthy glucose level for the patient and the physician is imminently reimbursed by the patient's HCP for such maintenance.

In one example, the disclosure describes a system, device, and a method for therapy delivery. In one example, the system comprises a delivery device configured to execute therapy information for directing the therapy delivery for a patient, wherein the therapy information comprises a treatment schedule specifying one or more treatments over a time period, wherein for each of the one or more treatments, the therapy information comprises a treatment type and a treatment amount; and processing circuitry communicably coupled to the delivery device, the processing circuitry configured to: determine a modification to the therapy information based on a recommendation of a digital twin, wherein the digital twin determines an estimated glucose level expected to be within a healthy range if the delivery device executes the modification to therapy information; and in response to physician review of the modification to the therapy information, output, to a healthcare provider system for the patient, data indicating completion of a healthcare service corresponding to the physician review.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
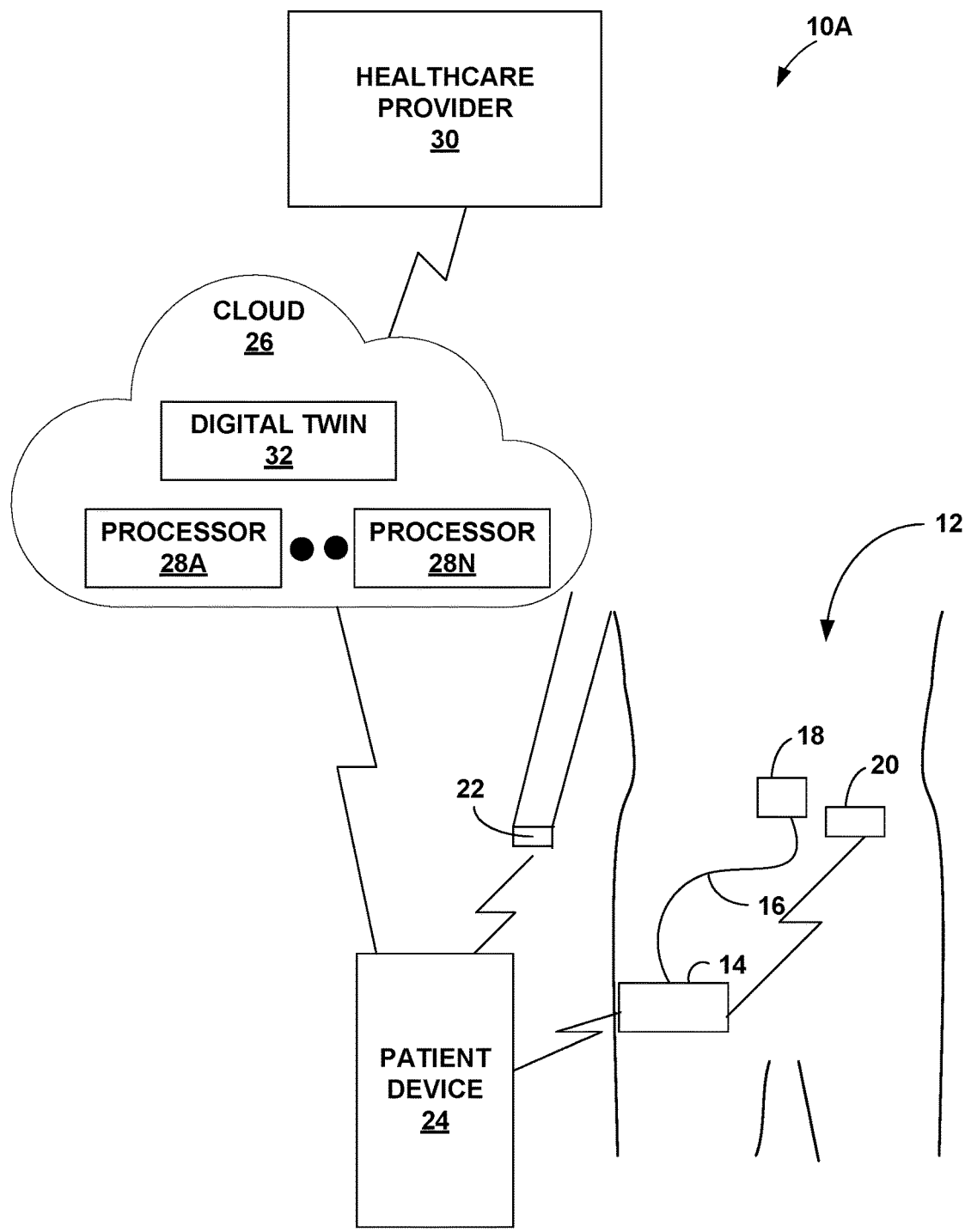
FIG. 1 is a block diagram illustrating an example system for delivering or guiding therapy dosage, in accordance with one or more examples described in this disclosure.

Devices, systems, and techniques for managing a glucose level in a patient are described in this disclosure. As described herein, examples of the devices, systems, and techniques may coordinate—on behalf of the patient, the patient's physician, or both the patient and the patient's physician—the patient's healthcare and/or therapy (e.g., for the patient's diabetes) between a number of separate systems. The examples of the devices, systems, and techniques enable a physician review of the patient's current healthcare and/or therapy, which may result in the patient receiving a better treatment (e.g., for diabetes). Some examples coordinate the physician review between the physician's device, a healthcare provider system, and another other entity involved in the patient's healthcare and/or therapy. Among the various reasons behind a lack of coordination in examples of conventional devices, systems, and techniques, differences between medical fields—in particular, the specialized healthcare services each provides—adds layers of complexity to each related task of the patient's healthcare and therapy (e.g., precluding the physician review from occurring and/or resulting in inefficient or non-existent healthcare service billing). In addition to coordinating the physician review and submitting bills for services rendered, a number of other aspects of healthcare management may be negatively affected by the lack of coordination in the conventional examples.

To illustrate by way of the following examples, the additional complexity may manifest in extraneous forms/documents, codes, and/or procedures for the physician to successfully complete before payment can be made for rendered health care services on the patient. The physician may perform most (if not all) of a healthcare service on the patient but may be unable to bill for that service (without great difficulty) and, in some instances, may decide to forego billing entirely, resulting in lost revenue. Even if the physician was successful in submitted the bill to the patient's HealthCare Provider (HCP), the HCP's system may reject the bill for trivial errors in procedure and/or substance.

To overcome or mitigate the lack of coordination in conventional examples, retrieve lost income for the physician, and/or open new revenue sources from performing healthcare services, the examples described herein may avail cloud/network services that are configured to remotely monitor at least one aspect of the patient's physiology (e.g., blood sugar or glucose level) and delivery some form of therapy. In some examples, the remote monitoring/delivery services may function as a bridge connecting HCP to the physician's device(s). Examples described herein may leverage a remote monitoring/delivery service, such as MEDTRONIC® CareLink™ or another entity capable of monitoring at least one aspect of the patient's physiology (e.g., diabetes health and management). Some remote monitoring/delivery services have client applications running in the physician's device(s) to communicate various sensor data corresponding to the patient's physiology. In other examples, the physician's devices (including wearable devices) may be programmed to periodically upload various sensor data.

As described herein, the examples described herein may instrument the patient with one or more sensors to measure the patient's glucose level and other diabetes-related data and have that information returned to the remote monitoring/delivery service for collection and analysis. The remote monitoring/delivery service may employ digital twin technology to build a representative model (i.e., "a digital twin") of the patient's physiological response to diabetes treatments. Some techniques may use the digital twin to determine an estimated glucose level for a current/next treatment (e.g., current/next treatment schedule, amount, and/or type). If that estimate is not within a healthy range of glucose levels, some devices, systems, and techniques described herein may modify the current treatment such that the digital twin updates the estimated glucose level to a healthy one. For example, the digital twin may determine new therapy information (e.g., for physician approval) that are predicted to result in keeping glucose level within a healthy range (e.g., between 70 to 180 mg/dl) based on received patient data indicating that the current therapy settings result in glucose levels that are not within the healthy range.

Some example devices, systems, and techniques described herein may present the modified treatment (e.g., modified treatment schedule, amount, and/or type) to the patient's physician as a query and based on the physician's response, may revert the modified treatment back to the current treatment in response to the physician rejection, correct the modified treatment in response to the physician correction, or accept the modified treatment in response to the physician approval.

If the physician corrected or approved the modified treatment, some examples may instruct the remote monitoring/delivery service to administer the corrected or modified treatment (e.g., via a delivery device) to the patient for improved therapy. By doing so, the physician has performed a healthcare service on the patient but conventional devices, systems, and techniques either are unable to or make it difficult to register a completion (or another event) of the healthcare service. As one reason, conventional examples of devices, systems, and techniques have never been configured for reimbursement of remote monitoring/delivery services. While some conventional examples automatically reject requests for remote monitoring/delivery reimbursement, other conventional examples may establish a substantial burden to obtain HCP approval for such requests (e.g., especially for diabetic patients). Due to the detailed and complex nature of some remote healthcare monitoring and/or delivery services, the HCP's requirements for approving these services may be too nuanced, causing the HCP to reject a substantial number requests for remote monitoring reimbursement. In other examples, the HCP's submission platform may be too sensitive, also resulting in a substantial number of rejections. A physician using the conventional techniques may have to spend a considerable amount of time with the HCP before the HCP approves even one reimbursement request. Because the physician could have spent the same time caring for his/her patients, the physician wastes the considerable time spent operating the conventional techniques.

The medical community defines a risk the physician takes on relative to benefit as Risk-Benefit Units (RBUs) and for each healthcare service, measure a number of RBUs. Because some medical fields have lower RBUs, the HCP may not have codified the particular healthcare service(s) in these medical fields. Furthermore, the HCP may not have any information regarding a particular healthcare service, cannot ascertain a value for that particular healthcare service, and therefore, cannot determine an adequate amount to reimburse the physician.

The examples described herein eliminate that inability or difficulty by automatically communicating, to the healthcare provider's system, information indicating the completion of or an event corresponding to performance of a critical healthcare service. As an example, the digital twin may produce a recommendation as to a proper diabetes therapy for a patient current receiving one or more treatments in accordance with a treatment schedule where each treatment has a treatment amount and treatment type. The recommendation may include a modification to the treatment schedule and/or to a treatment amount and/or treatment type for any number of the one or more treatments. The patient's physician may review a modified treatment schedule, a modified treatment amount, and/or a modified treatment and communicate data indicating the physician's approval, rejection, or correction, some examples automatically communicate, to the healthcare provider's system, information indicating the completion of the physician review. Other examples may automatically communicate such information upon the administration of the corrected or modified treatment. In response to receiving such information, the healthcare provider system may store data (e.g., a database record) memorializing the completion of or the event corresponding to performance of the healthcare service (e.g., the physician reviewing and modifying the recommended diabetes therapy) and, in turn, the patient (or the patient's insurance company) is billed and the physician is reimbursed for the healthcare service.

Some examples may, on behalf of the physician, automate reimbursement processing by submitting reimbursement requests and other data to the healthcare provider system for each instance where that physician performs the healthcare service. Some devices, systems, and techniques may generate messages with embedded invoices for communication to the healthcare provider system as part of an evidentiary submission that a reimbursable healthcare service has been rendered. To the benefit of the physician, some examples may ensure acceptance of the invoice by the healthcare provider by automatically populating each invoice with correct information showing that the tasks associated with an appropriate code for identifying the particular healthcare service performed on the patient is satisfied. In some examples, the healthcare provider system may assign a specific healthcare service code to a physician review/response of the patient's diabetes therapy; however, without evidence of satisfactory completion of that physician review/response, the healthcare provider system may cannot submit that code in a reimbursement request to the entity ultimately paying for the healthcare service, resulting in a rejection of the invoice, missing data from the patient's healthcare record, lost revenue for the physician, and other problems. The invoice may also include a full name of the patient, and/or the physician identifier assigned by the healthcare provider system. In conventional examples, the specific healthcare service code may not be available and/or buried in the healthcare provider's materials and because that code is not submitted to the healthcare provider system, the healthcare provider system rejects the invoice.

In some examples described herein, a cloud-based computing system may include a network device and one or more processors to automatically submit reimbursement requests for healthcare services related to physician review of the patient's diabetes therapy and each requested submission may be in response to receiving the physician's approval, rejection, and/or correction of a proposed (e.g., modified) treatment schedule and/or for one or more treatments, a proposed (e.g., modified) treatment amount, and/or treatment type. In some examples of the cloud-based system, the network device may access sensor data provided by various sensor devices measuring the patient's physiology. This data may be communicated directly to the cloud-based system or may be communicated to the remote monitoring/delivery service for storage. The network device may identify glucose level measurements in the sensor data, and if a measured glucose level is unhealthy for the patient, the network device may communicate a query to the physician requesting review of a modified insulin injection schedule, and/or for one or more treatments, a modified insulin amount and/or a modified insulin type. In some examples, the patient's digital twin may recommend the modified insulin injection schedule, and/or for one or more treatments, the modified insulin amount and/or the modified insulin type that, if implemented by the delivery device, may increase or decrease the patient's glucose level to a healthy one. Based on the patient's medical history and physiological data, the patient digital twin may determine an estimated glucose level if the patient discontinues the current insulin injection schedule, current insulin amount, and/or current insulin type and the delivery device applies new therapy settings for administering the modified insulin injection schedule, and/or for one or more treatments, the modified insulin amount and/or modified insulin type.

In some examples, the network device may periodically (e.g., every month) access the patient's glucose level from a patient device and/or the remote monitoring/delivery system and evaluate an effectiveness of the current insulin injection schedule, current insulin amount, and/or current insulin type. If the network device determines that a different diabetes therapy is needed to maintain the patient's glucose level within a healthy range, the network device may query the physician via a physician device. In some examples, the network device may modify the current insulin injection schedule, current insulin amount, and/or current insulin type to increase or decrease the patient's current glucose level to a healthy level and present such modification(s) on the physician device. The physician may review the modified insulin injection schedule, modified insulin amount, and/or modified insulin type and then, communicate, to the network device, a response indicating physician approval, physician correction (e.g., further modifying the proposed insulin therapy), or physician rejection of the modification(s).

In turn, the network device may automatically generate an invoice requesting reimbursement for the above-mentioned physician review and submit that invoice to the healthcare provider system. To effectuate a modified/corrected insulin injection schedule, insulin amount, and/or insulin type, the network device may communicate appropriate instructions directing the patient device and/or the delivery device, for example, to apply suitable delivery device settings. If the patient utilizes an insulin pump for diabetes therapy delivery, the insulin pump may apply the suitable device settings and, at a next insulin injection, deliver a dose of the modified/corrected insulin amount and/or insulin type according to the modified/corrected insulin injection schedule.

Some examples may program the delivery device to execute the patient's diabetes therapy, for example, to maintain the patient's glucose level to a healthy range. Absent physician input, the delivery device may execute device settings configured to provide a default diabetes treatment (e.g., a default treatment schedule, a default treatment amount, and/or a default treatment type). Some examples may be configured to estimate an amount the patient's glucose level is expected to increase or decrease in response to a current or proposed diabetes therapy. Based on the estimated increase/decrease to the patient's glucose level, some examples may determine whether to continue treating the patient's diabetes in accordance with the current diabetes therapy, to plan future treatments in accordance the proposed diabetes therapy, or to calibrate the current or proposed diabetes therapy (e.g., by fine-tuning a treatment schedule, a treatment amount, and/or a treatment type over a number of future treatments). Applying any new or different diabetes therapy may involve overriding default or current delivery device settings (e.g., in order to replace the current diabetes therapy with the proposed diabetes therapy). Over time, the examples described herein may modify the patient's diabetes treatments a number of times to determine an appropriate therapy configured to bring the patient's glucose level to a healthy glucose level. Some examples may continuously calibrate the treatment schedule, treatment amount, and/or treatment type until these parameters converge on an appropriate treatment schedule, an appropriate treatment amount, and/or an appropriate treatment type for maintaining the healthy glucose level.

As another benefit, the examples described above may coordinate healthcare service management amongst the patient's device(s), the physician's device(s), and devices in the cloud such that the patient receives a most effective treatment for diabetes. Some examples facilitate reimbursement payments for the physician's benefit and by doing so, facilitate the healthcare services for the patient's benefit. If the physician's time is no longer consumed with healthcare management (e.g., reimbursement requests), the physician may spend more time providing the patient with quality healthcare services. In addition to improved healthcare management, the patient may benefit from the devices, systems, and techniques described above preventing the negative effects of unhealthy glucose levels. For instance, by calibrating the patient's diabetes therapy based on the patient's digital twin, some examples may prevent hypoglycemia and/or hyperglycemia—where ineffective and/or insufficient treatments (e.g., insulin dosages) results in low or high glucose levels, respectively. Although the present disclosure often refers to insulin as the diabetes treatment, the examples may apply to the other medications.

FIG. 1 is a block diagram illustrating an example system for delivering or guiding therapy dosage, in accordance with one or more examples described in this disclosure. FIG. 1 illustrates system 10A that includes patient 12, insulin pump 14, tubing 16, infusion set 18, continuous glucose monitor (CGM) 20, wearable device 22, patient device 24, and cloud 26. Cloud 26 represents a local, wide area or global computing network including one or more processors 28A-28N ("one or more processors 28"). The present disclosure may in certain instances describe patient 12's glucose level as "blood sugar" and vice versa.

The example system may coordinate, on behalf of a physician, patient 12's healthcare and therapy (e.g., diabetes therapy) between a number of separate entities. In general, patient healthcare in most countries may involve several (e.g., at least three) entities, each of which may operate a computing systems of a single device or a number of devices to handle various tasks related to healthcare services for each patient and a number of mechanisms to maintain patient privacy while handling those tasks (e.g., administrative tasks, medical tasks, and/or the like). This is true for both remote and in-patient healthcare services. One independent system, healthcare provider 30, may represent a data platform operative to facilitate the administrative tasks for when healthcare services are provided between the physician and the patient. Instead of physical paperwork, physicians may provide healthcare provider 30, via the platform, with various data files (e.g., forms and/or documents) in performance of the administrative tasks; health care service billing, one example administrative task, may require patient 12's data (e.g., patient 12's identity), healthcare service data (e.g., service date, cost, and/or the like), and satisfactory proof or evidence of the actual service.

In some examples, the example system of FIG. 1 may automate reimbursement request submissions to healthcare provider 30 by generating the necessary documents and/or forms each time the physician provides patient 12 with a healthcare service to treat patient 12's diabetes. As described herein, the example system may build digital twin 32 to include a model configured to estimate patient 12's glucose level and employ a remote monitoring/delivery service to control patient 12's glucose level. In some examples, the example system may use the digital twin 32 to determine patient 12's estimated glucose level for patient 12's current diabetes therapy and in other examples, the example system may access patient 12's current glucose level. In both examples, the example system may use the digital twin 32 to propose a modified treatment schedule, amount, and/or type likely to bring the estimated or current glucose level to a healthy level. When the physician for patient 12 is requested to review the patient's current or proposed therapy, the physician may approve, rejection, or correct patient 12's current or modified diabetes treatment schedule, amount, and/or type. Upon receiving the physician's approval, rejection, or correction, the example system automatically generates an invoice requesting reimbursement from healthcare provider 30.

Patient 12 may be diabetic (e.g., Type 1 diabetic or Type 2 diabetic), and therefore, the glucose level in patient 12 may be uncontrolled without delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. CGM 20 may also be coupled to patient 12 to measure glucose level in patient 12. Insulin pump 14, tubing 16, infusion set 18, and CGM 20 may together form an insulin pump system. One example of the insulin pump system is the MINIMED™ 670G INSULIN PUMP SYSTEM by Medtronic, Inc. However, other examples of insulin pump systems may be used and the example techniques should not be considered limited to the MINIMED™ 670G INSULIN PUMP SYSTEM.

Insulin pump 14 may be a relatively small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places and patient 12 may place insulin pump 14 in a location based on the particular clothes patient 12 is wearing.

To deliver insulin, insulin pump 14 includes one or more reservoirs (e.g., two reservoirs). A reservoir may be a plastic cartridge that holds up to N units of insulin (e.g., up to 300 units of insulin) and is locked into insulin pump 14. Insulin pump 14 may be a battery powered device that is powered by replaceable and/or rechargeable batteries.

Tubing 16, sometimes called a catheter, connects on a first end to a reservoir in insulin pump 14 and connects on a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin travels from the reservoir of insulin pump 14, through tubing 16, and through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12. In some examples, insulin pump 14, tubing 16, infusion set 18, and/or sensor 20 may be contained in the same housing.

CGM 20 may include a sensor that is inserted under the skin of patient 12, such as near the stomach of patient 12 or in the arm of patient 12 (e.g., subcutaneous connection). The sensor of CGM 20 may be configured to measure the interstitial glucose level, which is the glucose found in the fluid between the cells of patient 12. CGM 20 may be configured to continuously or periodically sample the glucose level and rate of change of the glucose level over time.

In one or more examples, insulin pump 14 and CGM 20 may together form a closed-loop therapy delivery system with a remote monitoring/delivery service running in cloud 26. For example, patient 12 may set a target glucose level, usually measured in units of milligrams per deciliter, to insulin pump 14. Insulin pump 14 and/or the remote monitoring/delivery service of cloud 26 may receive the current glucose level from CGM 20, and in response may increase or decrease the amount of insulin delivered to patient 12. For example, if the current glucose level is higher than the target glucose level, insulin pump 14 and/or the remote monitoring/delivery service of cloud 26 may increase the insulin. If the current glucose level is lower than the target glucose level, insulin pump 14 and/or the remote monitoring/delivery service of cloud 26 may temporarily cease delivery of the insulin.

Insulin pump 14 and/or the remote monitoring/delivery service of cloud 26 may be considered as an example of an automated insulin delivery (AID) system. For example, insulin pump 14 and CGM 20 may be controlled by the remote monitoring/delivery service running in cloud 26. As described herein, digital twin 2 may propose a recommended therapy for patient 12. CGM 20 may communicate, to the remote monitoring/delivery service running in cloud 26, glucose level readings and by invoking digital twin 32, the remote monitoring/delivery service may determine a modification to patient 12's therapy based on a recommendation of digital twin 32. In some examples, the remote monitoring/delivery service may determine a modified treatment schedule and/or for one or more (future) treatments, a modified treatment amount and/or a modified treatment type and to effectuate the modification, may communicate, to patient device 24, instructions directing insulin pump 14 to apply the modified treatment schedule, amount, and/or type.

For example, insulin pump 14, CGM 20, and the remote monitoring/delivery service running in cloud 26 may be configured to operate together to mimic some of the ways in which a healthy pancreas works. Insulin pump 14 may be configured to deliver basal insulin, which is a small amount of insulin released continuously throughout the day. There may be times when glucose levels increase, such as due to eating or some other activity that patient 12 undertakes. Insulin pump 14 may be configured to deliver bolus insulin on demand in association with food intake or to correct an undesirably high glucose level in the bloodstream. In one or more examples, if the glucose level rises above a target level, then insulin pump 14 may increase the bolus insulin to address the increase in glucose level. Insulin pump 14 may be configured to compute basal and bolus insulin delivery, and deliver the basal and bolus insulin accordingly. For instance, insulin pump 14 may determine the amount of basal insulin to deliver continuously, and then determine the amount of bolus insulin to deliver to reduce glucose level in response to an increase in glucose level due to eating or some other event.

Accordingly, in some examples, CGM 20 may sample glucose level and rate of change in glucose level over time. CGM 20 may output the glucose level to insulin pump 14 (e.g., through a wireless link connection like Bluetooth). Insulin pump 14 may compare the glucose level to a target glucose level (e.g., as set by patient 12 or clinician), and adjust the insulin dosage based on the comparison.

As described above, patient 12 or a clinician may set the target glucose level on insulin pump 14. There may be various ways in which patient 12 or the clinician may set the target glucose level on insulin pump 14. As one example, patient 12 or the clinician may utilize patient device 24 to communicate with insulin pump 14. Examples of patient device 24 include mobile devices, such as smartphones or tablet computers, laptop computers, and the like. In some examples, patient device 24 may be a special programmer or controller for insulin pump 14. Although FIG. 1 illustrates one patient device 24, in some examples, there may be a plurality of patient devices. For instance, system 10A may include a mobile device and a controller, each of which are examples of patient device 24. For ease of description only, the example techniques are described with respect to patient device 24, with the understanding that patient device 24 may be one or more patient devices.

Patient device 24 may also be configured to interface with CGM 20. As one example, patient device 24 may receive information (e.g., glucose level or rate of change of glucose level) directly from CGM 20 (e.g., through a wireless link). As another example, patient device 24 may receive information from CGM 20 through insulin pump 14, where insulin pump 14 relays the information between patient device 24 and CGM 20.

In one or more examples, patient device 24 may display a user interface with which patient 12 or the clinician may control insulin pump 14. For example, patient device 24 may display a screen that allows patient 12 or the clinician to enter the target glucose level. As another example, patient device 24 may display a screen that outputs the current glucose level. In some examples, patient device 24 may output notifications to patient 12, such as notifications if the glucose level is too high or too low, as well as notifications regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through patient device 24 is one example, and should not be considered limiting. For example, insulin pump 14 may include a user interface (e.g., pushbuttons) that allow patient 12 or the clinician to set the various glucose levels of insulin pump 14. Also, in some examples, insulin pump 14 itself, or in addition to patient device 24, may be configured to output notifications to patient 12. For instance, if the glucose level is too high or too low, insulin pump 14 may output an audible or haptic output. As another example, if the battery is low, then insulin pump 14 may output a low battery indication on a display of insulin pump 14.

The above describes examples ways in which insulin pump 14 may deliver insulin to patient 12 based on the current glucose levels (e.g., as measured by CGM 20). In some cases, there may be therapeutic gains by proactively delivering insulin to patient 12, rather than reacting to when glucose levels become too high or too low.

The glucose level in patient 12 may increase due to particular user actions (or user inactivity). As one example, the glucose level in patient 12 may increase due to patient 12 engaging in an activity like eating or exercising. In some examples, there may be therapeutic gains if it is possible to determine that patient 12 is engaging in the activity, and delivering insulin based on the determination that patient 12 is engaging in the activity.

For example, patient 12 may forget to cause insulin pump 14 to deliver insulin after eating, resulting an insulin shortfall. Alternatively, patient 12 may cause insulin pump 14 to deliver insulin after eating but may have forgotten that patient 12 previously caused insulin pump 14 to deliver insulin for the same meal event, resulting in an excessive insulin dosage. Also, in examples where CGM 20 is utilized, insulin pump 14 may not take any action until after the glucose level is greater than a target level. By proactively determining that patient 12 is engaging in an activity, insulin pump 14 may be able to deliver insulin in such a manner that the glucose level does not rise above the target level or rises only slightly above the target level (i.e., rises by less than what the glucose level would have risen if insulin were not delivered proactively). In some cases, by proactively determining that patient 12 is engaging in an activity and delivering insulin accordingly, the glucose level of patient 12 may increase more slowly.

As illustrated, patient 12 may wear wearable device 22. Examples of wearable device 22 include a smartwatch or a fitness tracker, either of which may, in some examples, be configured to be worn on a patient's wrist or arm. In one or more examples, wearable device 22 includes one or more accelerometers (e.g., a six-axis accelerometer). Wearable device 22 may be configured to determine one or more movement characteristics of patient 12. Examples of the one or more movement characteristics include values relating to frequency, amplitude, trajectory, position, velocity, acceleration and/or pattern of movement instantaneously or over time. The frequency of movement of the patient's arm may refer to how many times patient 12 repeated a movement within a certain time (e.g., such as frequency of movement back and forth between two positions).

Patient 12 may wear wearable device 22 on his or her wrist. However, the example techniques are not so limited. Patient 12 may wear wearable device 22 on a finger, forearm, or bicep. In general, patient 12 may wear wearable device 22 anywhere that can be used to determine gestures indicative of eating, such as movement characteristics of the arm.

As illustrated in FIG. 1, system 10A includes cloud 26 that includes one or more processors 28. Cloud 26 represents a cloud infrastructure that supports one or more processors 28 on which applications or operations requested by one or more users run. For example, cloud 26 provides cloud computing for using one or more processors 28, to store, manage, and process data, rather than by personal device 24 or wearable device 22. One or more processors 28 may share data or resources for performing computations, and may be part of computing servers, web servers, database servers, and the like. One or more processors 28 may be in servers within a datacenter or may be distributed across multiple datacenters. In some cases, the datacenters may be in different geographical locations.

One or more processors 28, as well as other processing circuitry described herein, can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed one or more processors 28, as well as other processing circuitry described herein, herein may be embodied as hardware, firmware, software or any combination thereof.

One or more processors 28 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. One or more processors 28 may include arithmetic logic units (ALUs), elementary function units (EFUs), digital circuits, analog circuits, and/or programmable cores, formed from programmable circuits. In examples where the operations of one or more processors 28 are performed using software executed by the programmable circuits, memory (e.g., on the servers) accessible by one or more processors 28 may store the object code of the software that one or more processors 28 receive and execute.

In some examples, one or more processors 28 may be configured to determine patterns from gesture movements (e.g., as one or more movement characteristics determined by wearable device 22), and configured to determine a particular activity patient 12 is undertaking. One or more processors 28 may provide responsive real-time cloud services that can, on a responsive real-time basis, determine the activity patient 12 is undertaking, and in some examples, provide recommended therapy (e.g., insulin dosage amount). Cloud 26 and patient device 24 may communicate via Wi-Fi or through a carrier network.

In general, feedback and modeling via digital twin 32 may impact patient 12's healthcare services. Parameters, settings, and/or other configuration information can be pre-determined for the patient 12 and a particular procedure based on modeling via digital twin 32, for example. Prescription(s), laboratory test(s), referral(s), etc., can be driven via the digital twin 32, alone or in conjunction with patient 12 and/or provider feedback, for example. In certain examples, data mining, modeling, prediction, other probabilities, etc., generated for the particular patient 12 via the digital twin 32 can be extrapolated (and anonymized) for an associated or similar population. Thus, patient 12's experience can help to improve health care experiences for a plurality of similar patients (e.g., by relation, geographic area, body type, condition, employment, race, gender, and/or the like).

In some examples, one or more processors 28 may be configured to determine an amount of insulin (e.g., therapy dosage of bolus insulin) to deliver to patient 12. As one example, memory accessible by one or more processors 28 may store patient parameters of patient 12 (e.g., weight, height, etc.). The memory may also store a look-up table that indicates an amount of bolus insulin that is to be delivered for different patient parameters and different types of foods. One or more processors 28 may access the memory and based on the type of food patient 12 is eating and patient parameters may determine the amount of bolus insulin that patient 12 is to receive.

As another example, one or more processors 28 may be configured to utilize a representative model or "digital twin" (e.g., digital twin 32) of patient 12 to determine a set of insulin pump 14 settings that are beneficial to patient 12 when applied to patient 12's therapy. Examples of such settings include carbohydrate ratios, basal insulin profiles, insulin sensitivity factors and active insulin time. These settings may be established or modified by the physician as part of a patient visit or via a remote monitoring service. Digital twin 32 may be a digital replica or model of patient 12. Digital twin 32 may be software executing on one or more processors 28. Digital twin 32 may receive, as input, information about what patient 12 is eating. Because digital twin 32 is a digital replica of patient 12, the output from digital twin 32 may be information about what the glucose level of patient 12 may be after eating, as well as a recommendation of how much bolus insulin to deliver to patient 12 to control the increase the glucose level. Accordingly, a digital twin 32 of patient 12 allows analysis of real-time data (e.g., what patient 12 is eating), impact on patient 12 (e.g., how much change there will be in the glucose level), and/or therapy recommendations (e.g., how much insulin to provide). Some therapy recommendations may indicate modifications to patient 12's current therapy.

For example, when patient 12 is about to eat they would estimate as an amount of carbs in their meal, patient 12 may enter that carbohydrate estimate into digital twin 32 via one or more processors 28, which operates insulin pump 14's bolus calculator. In turn, one or more processors 28 may use the carbohydrate estimate entry along with the carbohydrate ratio setting to determine an actual amount of bolus insulin that should be delivered to cover the meal.

One or more processors 28 may automatically, and with minimal input from patient 12, determine that patient 12 is undertaking a particular activity, and determine an amount of basal insulin to deliver based on the determination. In response to the particular activity (e.g., aerobic exercise), one or more processors 28 may suppress or limit bolus insulin delivery (e.g., via insulin pump 14) during the particular activity given that the particular activity is likely to make patient 12's glucose level fall. One or more processors 28 may output the recommendation of the amount of basal or bolus insulin to deliver to patient device 24. Patient device 24, may then in turn, control insulin pump 14 to deliver the determined amount of basal or bolus insulin. As one example, patient device 24 may output to insulin pump 14 the amount of basal or bolus insulin to deliver. As another example, patient device 24 may output a target glucose level, and insulin pump 14 may deliver the appropriate insulin amount and/or type to achieve the target glucose level. In some examples, it may be possible for one or more processors 28 to output to patient device 24 information indicative of the target glucose level, and patient device 24 may output that information to insulin pump 14. All of these examples may be considered as examples of one or more processors 28 determining an amount of insulin to deliver to patient 12.

There are a number of ways of determining whether patient 12 is undertaking an activity, determining an amount of insulin to deliver, and causing the amount of insulin to be delivered. In this manner, there is an increase in likelihood that patient 12 will receive the correct amount of dosage of insulin at the right time, and decrease in likelihood of human error causing issues (e.g., patient 12 forgetting to log meals, forgetting to take insulin, or taking insulin but forgetting to have taken insulin). While the above examples may be beneficial in patient 12 receiving insulin at the right time, this disclosure describes example techniques to coordinate multiple independent systems to facilitate healthcare service management for patient 12.

As described herein, patient device 24, one or more network devices in cloud 26, healthcare provider 30, and a device for patient 12's physician, may cooperate to perform a healthcare service, for example, by sharing various data. In some examples, sensor devices (e.g., CGM 20 and other sensors) may be configured to sense different aspects of patient 12's physiology and store, in patient device 24, various sensor data generated by the sensor devices. In some examples, CGM 20 may capture and store glucose level readings in patient device 24 where these readings are available for access across a network (e.g., by cloud 26). For insulin pump 14 (or another example delivery device), patient device 24 may store therapy information for codifying patient 12's diabetes therapy (e.g., in terms of a current or historical treatment schedule (e.g., treatment date/time), amount, and/or type).

One or more processors 28 of cloud 26 may retrieve current or historical glucose level readings (e.g., in a feed) from patient device 24 and, based on such readings, build digital twin 32 to model patient 12's physiology (e.g., glucose level) in response to different treatments (e.g., different combinations of treatment schedule, amount, and type). One or more processors 28 may identify a correlation between patient 12's current or historical treatment and patient 12's current or historical glucose level and, based on such a correlation, digital twin 32 may determine an estimated glucose level for if/when insulin pump 14 administers a modified treatment to patient 12. If the estimated glucose level is within a healthy range but the current or historical glucose level is not within that range (e.g., unhealthy), one or more processors 28 may generate a query to present the modified treatment for physician review and communicate that query to the physician's device. In some examples, one or more processors 28 may present, via a user interface (UI), content including the query and UI controls operative to communicate different physician responses (e.g., physician approval, rejection, or correction of the modified treatment).

As described herein, receiving any of the above physician responses may prompt one or more processors 28 to perform one or more actions. If the physician response is a rejection of the proposed modified treatment, one or more processors 28 may revert the modified treatment back to the current treatment and apply suitable device settings only if insulin pump 14 is not administering the current treatment. Otherwise, none of insulin pump 14's settings are modified. If the physician response is a correction of the modified treatment, one or more processors 28 may apply the corrected treatment by modifying insulin pump 14's settings in accordance with the physician response. Similarly, if the physician response is an approval of the modified treatment, one or more processors 28 may modify device settings on insulin pump 14 to replace the current treatment with the proposed modified treatment.

Providing the physician response may complete the physician review as a healthcare service, regardless of which physician response is provided. In some examples, the physician's device may include processing circuitry configured to provide the physician response and then, automatically submit, to healthcare provider 30, data indicating completion of the physician review or data indicating an event corresponding the patient. In other examples, as a response to receiving the physician response from the physician's device, one or more processors 28 may automatically submit, to healthcare provider 30, data indicating completion of the physician review or data indicating an event corresponding to patient 12. In some examples, one or more processors 28 may submit the physician response and/or other evidence of the completion of the physician review or the event corresponding to patient 12. In some examples, accompanying the above evidentiary submission to healthcare provider 30, one or more processors 28 may generate an invoice requesting from healthcare provider 30 reimbursement for the physician review. In some examples, one or more processors 28 may populate the invoice with information compatible with healthcare provider 30, which enables healthcare provider 30 to correctly bill patient 12 or patient 12's insurance company. In some examples, healthcare provider 30 may submit a form identifying the physician review as the healthcare service (e.g., a numeric code) and use the invoice as evidence of satisfactory completion of the physician review. Populating the invoice with compatible information may ensure healthcare provider 30 accepts the submission and patient 12's insurance company approves for reimbursement the physician review in the invoice.

However, in other examples, patient 12 may not have insulin pump 14. Rather, patient 12 may utilize a manual injection device (e.g., a syringe) to deliver insulin or an injection device (e.g., an insulin pen, sometimes also called a smart insulin pen, or an insulin pen with a smart cap where the smart cap can be used to set particular doses of insulin). For example, rather than insulin pump 14 automatically delivering insulin, patient 12 (or possible a caretaker of patient 12) may fill a syringe with insulin and inject himself or herself.

The above examples described insulin pump 14, a syringe, and the injection device as example ways in which to deliver insulin. In this disclosure, the term "insulin delivery device" may generally refer to a device used to deliver insulin. Examples of insulin delivery device include insulin pump 14, a syringe, and the injection device. As described, the syringe may be a device used to inject insulin but is not necessarily capable of communicating or dosing a particular amount of insulin. The injection device, however, may be a device used to inject insulin that may be capable of communicating with other devices or may be capable of dosing a particular amount of insulin. The injection device may be powered (e.g., battery powered) device, and the syringe may be device that requires no power.

Figure 2:
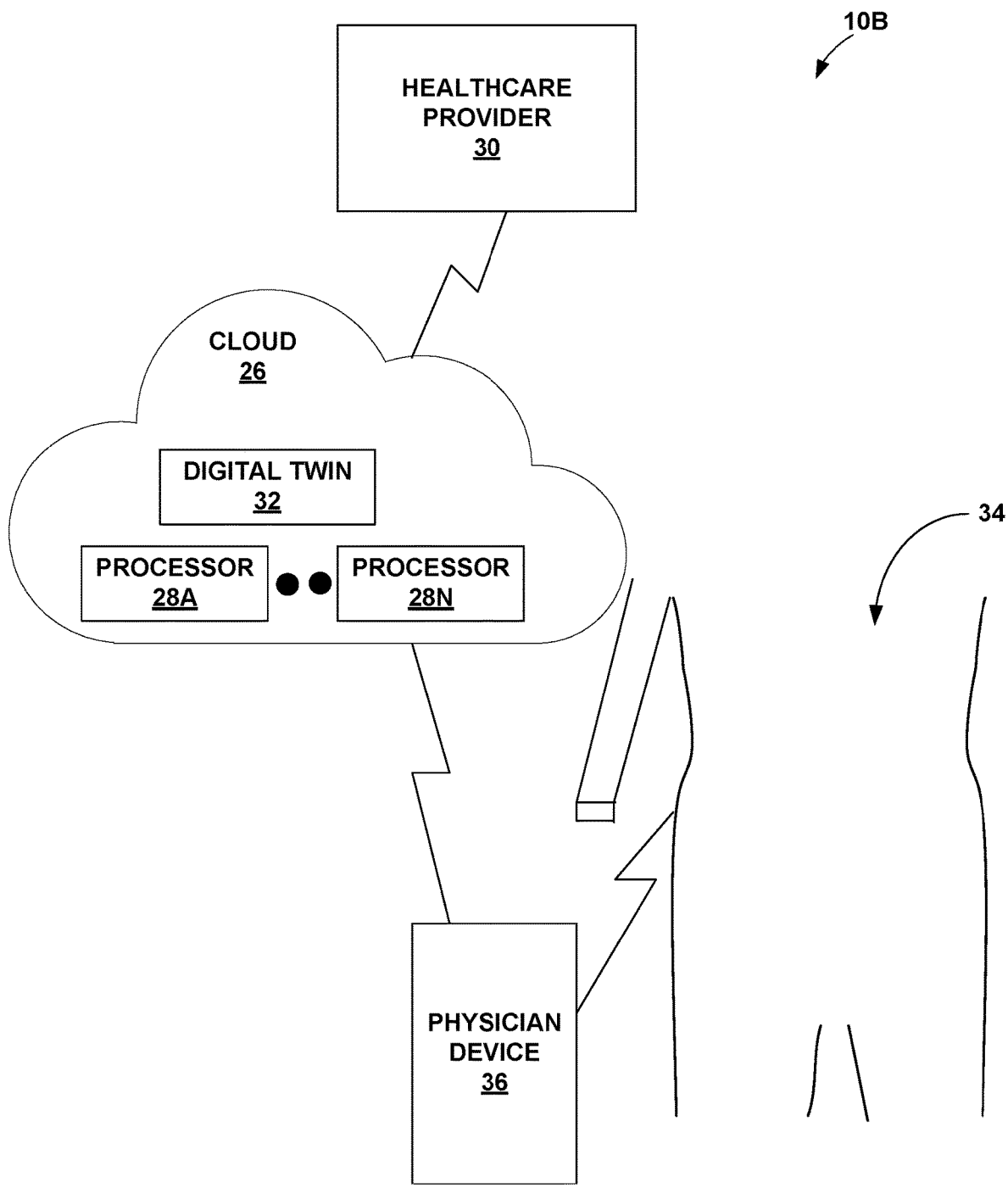
FIG. 2 is a block diagram illustrating another example system for delivering or guiding therapy dosage, in accordance with one or more examples described in this disclosure.

FIG. 2 is a block diagram illustrating another example system for delivering or guiding therapy dosage, in accordance with one or more examples described in this disclosure. In FIG. 2, physician 34 is patient 12's physician and given authority over patient 12's diabetes therapy. FIG. 2 illustrates system 10B that is from perspective of physician 34 while system 10A of FIG. 1 is from perspective of patient 12.

Physician 34 may utilize physician device 36 for a number of applications as described herein. Examples of physician device 36 may include computing and mobile devices (e.g., a smartphone) such as those described herein. In some examples, physician device 36 may generate a graphical user interface (e.g., a portal) to exchange information with cloud 26. Via the graphical user interface (GUI), physician device 36 may present information describing a proposed insulin treatment as set forth in a query that one or more processors 28 may have communicated. Physician 34 may use the GUI's functionality to review the proposed insulin treatment and return a response (e.g., a rejection, an approval, or a correction) to cloud 26. Physician 34 may use the GUI's functionality to juxtapose the proposed insulin treatment with other patient data (e.g., sensed physiological data). Upon receiving physician 34's response, one or more processors 28 may generate an invoice requesting reimbursement for physician 34's review of and response to the proposed insulin treatment.

Figure 3:
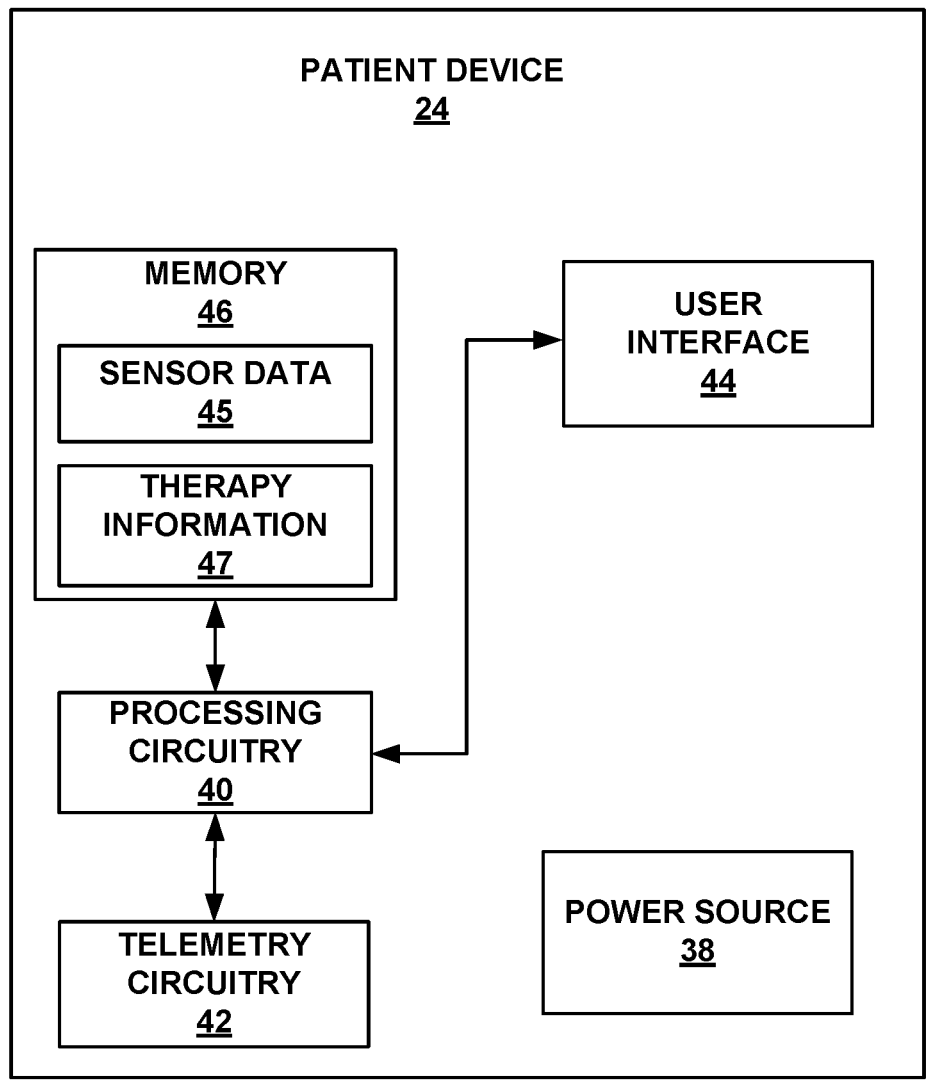
FIG. 3 is a block diagram illustrating an example of a patient device, in accordance with one or more examples described in this disclosure.

FIG. 3 is a block diagram illustrating an example of a patient device, in accordance with one or more examples described in this disclosure. While patient device 24 may generally be described as a hand-held computing device, patient device 24 may be a notebook computer, a cell phone, or a workstation (e.g., a desktop computer), for example. In some examples, patient device 24 may be a mobile device, such as a smartphone or a tablet computer. In such examples, patient device 24 may execute an application that allows patient device 24 to perform example techniques described in this disclosure. In some examples, patient device 24 may be specialized controller for communicating with insulin pump 14 (e.g., to program or to operate insulin pump 14).

Although the examples are described with one patient device 24, in some examples, patient device 24 may be a combination of different devices (e.g., mobile device and a controller). For instance, the mobile device may provide access to one or more processors 28 of cloud 26 through Wi-Fi or carrier network and the controller may provide access to insulin pump 14. In such examples, the mobile device and the controller may communicate with one another through Bluetooth or BLE. Various combinations of a mobile device and a controller together forming patient device 24 are possible and the example techniques should not be considered limited to any one particular configuration.

As illustrated in FIG. 3, patient device 24 may include power source 38, processing circuitry 40, telemetry circuitry 42, user interface 44, and memory 46. Memory 46 may store program instructions that, when executed by processing circuitry 40, cause processing circuitry 40 to provide the functionality ascribed to patient device 24 throughout this disclosure. Memory 46 may store various software applications to operate as clients for cloud-based services/network-based applications. As described herein, memory 46 may store a client for a remote monitoring/delivery service running in cloud 26 and/or a client for insulin pump 14 and/or another delivery device and in some instances, both clients combine to integrate their functionalities and capabilities.

In some examples, memory 46 of patient device 24 may store a plurality of parameters, such as amount and types of insulin to deliver, target glucose level, time(s) of delivery etc. Processing circuitry 40 (e.g., through telemetry circuitry 42) may output the parameters stored in memory 46 to insulin pump 14 or another delivery device (e.g., a "smart" injection device) for delivery of insulin to patient 12. In some examples, processing circuitry 40 may execute a notification application, stored in memory 46, that outputs notifications to patient 12, such as notification to take insulin, amount of insulin, and time to take the insulin, via user interface 44.

In some examples, memory 46 of patient device 24 may store sensor data 45 and therapy information 47. As described herein, patient 12 may be instrumented with one or more devices known as sensors for measuring patient physiological data including a sensor (e.g., CGM 20) configured to measure the patient's glucose level and other diabetes-related data. Processing circuitry 40 may store sensor data 45 in memory 46 and then, have that information returned to the remote monitoring/delivery service running in cloud 26. Other sensors may have that information returned to the remote monitoring/delivery service for collection and analysis. In some examples, the therapy information 47 specifies current and future treatments over a time period that when administered to patient 12, may be expected to maintain patient 12's glucose level within a healthy range. The remote monitoring/delivery service may push, onto patient device 24, suitable device settings and/or instructions for operating patient 12's delivery device and then, may have such information stored in memory 46 as therapy information 47. Processing circuitry 40 (e.g., executing the client application for the remote monitoring/delivery service) may receive/retrieve the suitable device settings and/or instructions and via telemetry circuitry 42, in turn, telemetry circuitry 42 may implement those settings and/or instructions on insulin pump 14 or another delivery device.

Memory 46 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 40 can take the form one or more microprocessors, DSPs, ASICs, FPGAs, programmable logic circuitry, or the like, and the functions attributed to processing circuitry 40 herein may be embodied as hardware, firmware, software or any combination thereof.

User interface 44 may include a button or keypad, lights, a speaker for voice commands, and a display, such as a liquid crystal (LCD). In some examples the display may be a touch screen. As discussed in this disclosure, processing circuitry 40 may present and receive information relating to therapy via user interface 44. For example, processing circuitry 40 may receive patient input via user interface 44. The patient input may be entered, for example, by pressing a button on a keypad, entering text, or selecting an icon from a touch screen. The patient input may be information indicative of food that patient 12 eats, such as for the initial learning phase, whether patient 12 took the insulin (e.g., through the syringe or injection device 30), and other such information.

Telemetry circuitry 42 includes any suitable hardware, firmware, software or any combination thereof for communicating with another device, such as cloud 26, insulin pump 14 or an injection device, as appliable, wearable device 22, and CGM 20. Telemetry circuitry 42 may receive communication with the aid of an antenna, which may be internal and/or external to patient device 24. Telemetry circuitry 42 may be configured to communicate with another computing device via wireless communication techniques, or direct communication through a wired connection. Examples of local wireless communication techniques that may be employed to facilitate communication between patient device 24 and another computing device include RF communication according to IEEE 802.11 or Bluetooth, or BLE specification sets, infrared communication, e.g., according to an IrDA standard, or other standard or proprietary telemetry protocols. Telemetry circuitry 42 may also provide connection with carrier network for access to cloud 26. In this manner, other devices may be capable of communicating with patient device 24.

Power source 38 delivers operating power to the components of patient device 24. In some examples, power source 38 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within patient device 24.

As described herein, patient device 24 may store sensor data 45 that may be generated using one or more sensor devices including historical and current glucose level readings captured by CGM 20. Telemetry circuitry 42 may communicate sensor data 45 to a cloud-based system, such as cloud 26 of FIGS. 1-2. In some examples, the cloud-based system provides patient device 24 with device settings and/or instructions for administering a treatment to patient 12. In some examples, telemetry circuitry 42 may apply the device settings to a delivery device, such as insulin pump 14 of FIGS. 1-2.

Figure 4:
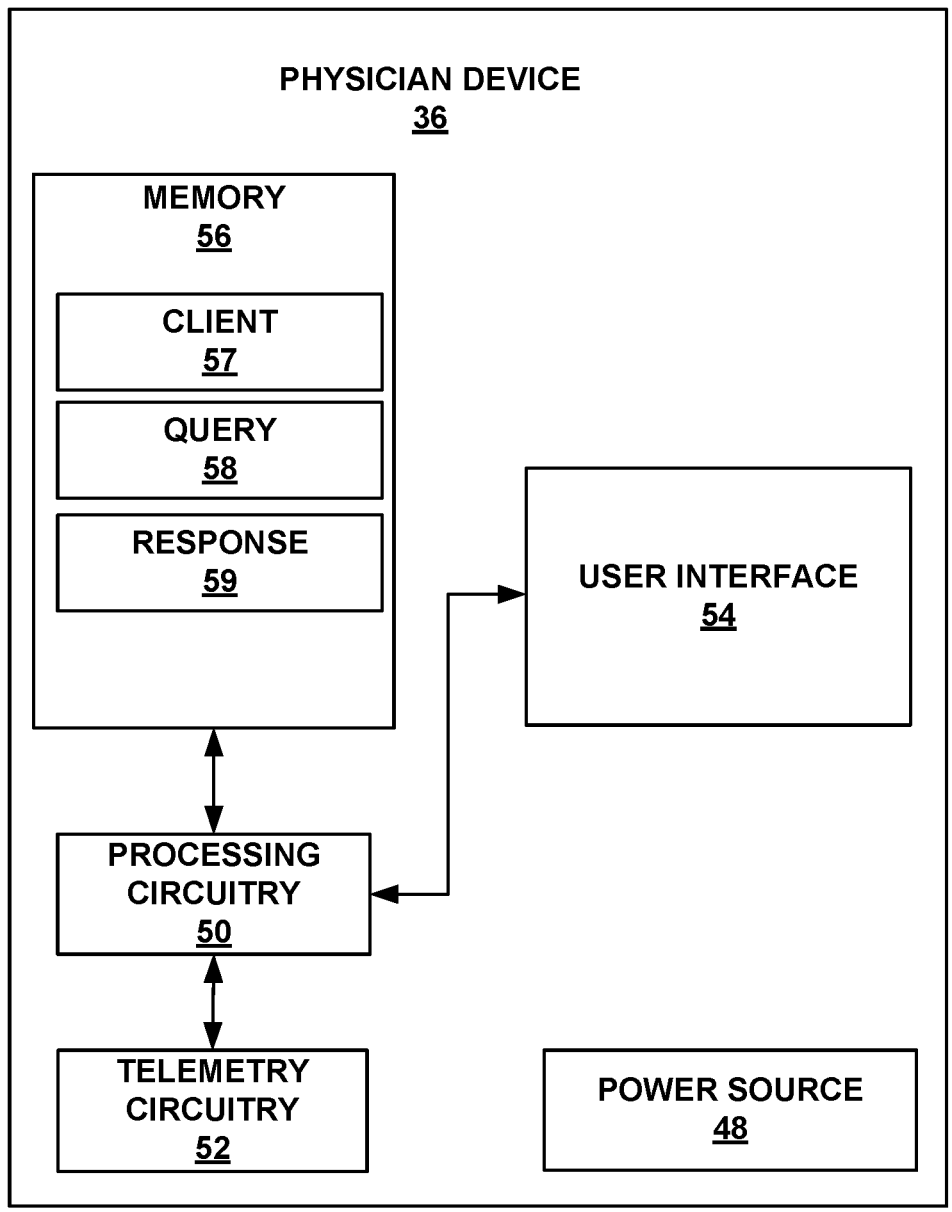
FIG. 4 is a block diagram illustrating an example of a physician device, in accordance with one or more examples described in this disclosure.

FIG. 4 is a block diagram illustrating an example of a physician device, in accordance with one or more examples described in this disclosure. While physician device 36 may generally be described as a hand-held computing device, physician device 36 may be a notebook computer, a cell phone, or a workstation, for example. In some examples, physician device 36 may be a mobile device, such as a smartphone or a tablet computer. In such examples, physician device 36 may execute an application that allows physician device 36 to perform example techniques described in this disclosure. In some examples, physician device 36 may be an authorized device to run a portal to a data platform in a cloud-based system such as cloud 26. One or more processors 28 of FIGS. 1-2 may run the data platform to automate various healthcare processes involving patient device 24 of FIGS. 1-3, healthcare provider 30, and physician device 36.

As illustrated, physician device 36 includes power source 48, processing circuitry 50, telemetry circuitry 52, user interface 54, and memory 56. Power source 48, processing circuitry 50, telemetry circuitry 52, user interface 54, and memory 56 may be similar to power source 38, processing circuitry 40, telemetry circuitry 42, user interface 44, and memory 46 of FIG. 3, respectively. Memory 56 stores one or more software application for processing circuitry 50 to execute, such as client 57. Client 57 may be a client application for generating the portal to the data platform in cloud 26. In some examples, client 57 generates the portal to present query 58 requesting physician review of patient 12's current or proposed diabetes therapy. Cloud 26 may communicate query 58 as part of a healthcare service. After reviewing a current or modified treatment for effectiveness, physician 34, via client 57, may output physician response 59 indicative of either a physician approval, rejection, or correction. Cloud 26 may receive physician input including physician response 59 and perform an action effectuating the physician approval, rejection, or correction. One example physician response 49 may specify a correct treatment schedule, and/or for one or more treatments, a correct treatment amount and/or a correct treatment type.

By doing so, physician 34, via cloud 26 and client 57, completes performance of the healthcare service and is permitted reimbursement by patient 12 and/or patient 12's insurance company. Physician 34 benefits from cloud 26 and client 57 automating reimbursement request submissions via healthcare provider 30 to patient 12 and/or patient 12's insurance company. As one benefit, physician 34 may advantageously take a hands-off approach to billing patient 12 and/or patient 12's insurance company. As another benefit, cloud 26 ensures that a reimbursement request satisfies each requirement set forth by healthcare provider 30, patient 12, and/or patient 12's insurance company. In some examples, patient 12 and/or patient 12's insurance company may outline requirements (e.g., for certain forms or documents) for accepting the reimbursement request via the portal and requirements (e.g., for certain codes and identifiers) for approving payment in satisfaction of the request. It should be noted that in some examples, another entity besides patient 12 may be responsible for (some if not all of) patient 12's healthcare and physician 34 may also benefit from cloud 26 and client 57 automating reimbursement request submissions to that entity.

Figure 5:
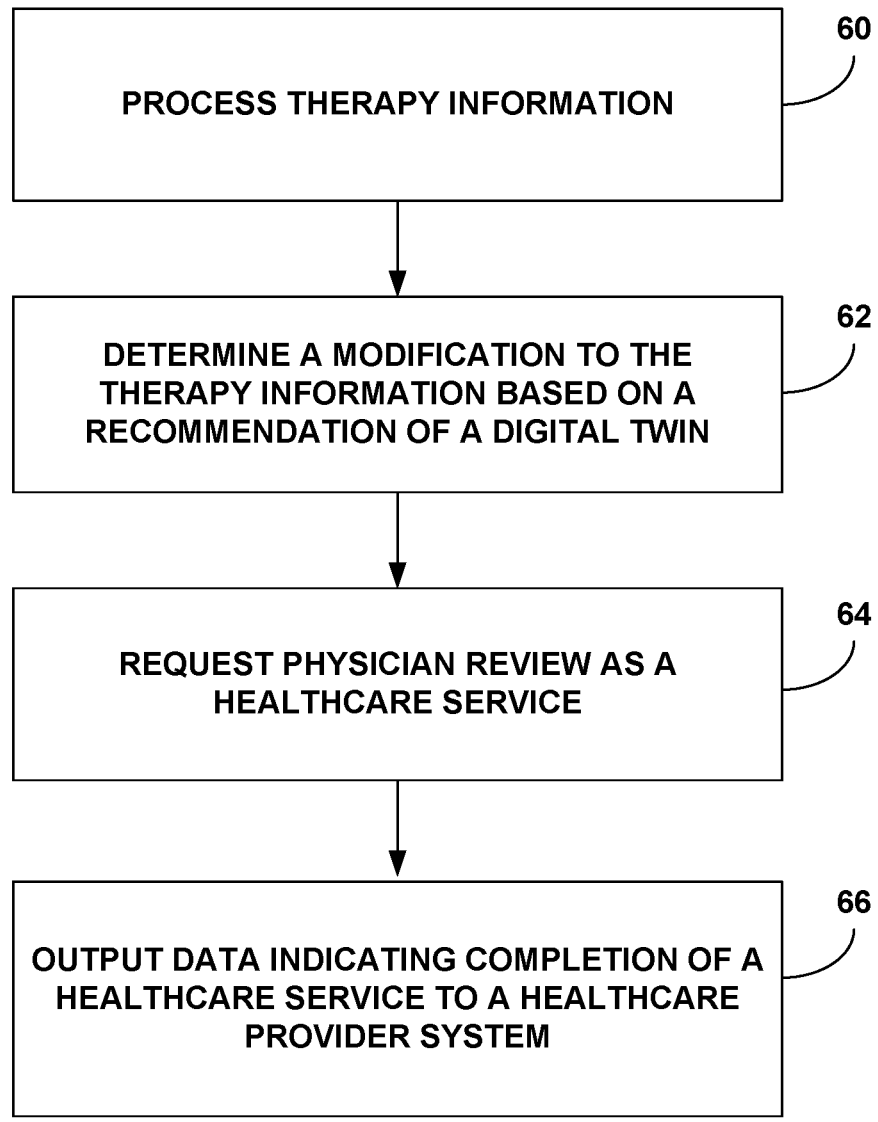
FIG. 5 is a flow diagram illustrating an example operation, in accordance with one or more examples described in this disclosure.

FIG. 5 is a flow diagram illustrating an example operation, in accordance with one or more examples described in this disclosure.

The one or more processors may process therapy information (60). As described herein, the therapy information may refer to a series of diabetes treatments (e.g., insulin dosages) that if administered correctly, is designed to maintain a health glucose level for patient 12. For each treatment, the therapy information may indicate a treatment date/time or frequency (e.g., a treatment schedule), a treatment amount, and a treatment type (e.g., an insulin type, such as bolus or basal insulin types). Depending on which delivery device patient 12 employs to delivery diabetes therapy, the therapy information may include appropriate device settings and/or instructions for administering each treatment. If the delivery device is an insulin pump such as insulin pump 14, one or more processors 28 of cloud 26 and/or processing circuitry 40 of patient device 24 may communicate a control directive instructing insulin pump 14 to replace current device settings with appropriate device settings for administrating at least one new treatment. If the delivery device is an injection device with a smart pen or a smart insulin pen, one or more processors 28 of cloud 26 and/or processing circuitry 40 of patient device 24 may communicate a control directive instructing the injection device with the smart pen or the smart insulin pen to prepare a next treatment for delivery to the patient at a particular date/time. In other examples, the control directive may instruct the injection device with the smart pen or the smart insulin pen to output information describing the at least one new treatment.

When properly administered to patient 12, at least one treatment in the therapy information may cause patient 12's glucose level to increase or decrease (to healthy or unhealthy levels). In some examples, the therapy information may include a treatment schedule specifying dates/times at which the delivery device may deliver various treatment amounts of one or more treatment types. The one or more processors may determine the glucose level of patient 12 at any point during the delivery device's execution of the therapy information. The one or more processors may determine the glucose level based on sensor data of patient 12; for example, CGM 20 may provide the one or more processors with historical and/or current glucose level readings. In other examples, the one or more processors may determine the glucose level based on a digital twin of patient 12. In some examples, the one or more processors may utilize both the digital twin of patient 12 and the sensor data of patient 12 to determine the glucose level. If the digital twin is used in determining the glucose level, the determined glucose level may be considered an estimate instead of a measurement; whereas, the glucose level solely based on the sensor data may be considered a measurement.

The one or more processors may determine a modification to the therapy information based on a recommendation of a digital twin (62). The digital twin may determine an estimated glucose level for a patient corresponding to the delivery device executing the modification to the therapy information. In some examples, the one or more processors may apply the digital twin to different treatments (e.g., different combinations of treatment dates/times (e.g., the treatment schedule), amounts, and/or types) and determine whether patient 12's current diabetes therapy can be improved by modifying current or next treatment dates/times (e.g., the treatment schedule), amounts, and/or types. If the digital twin indicates a healthy glucose level (e.g., within a healthy range) that is likely to result from implementing a modified treatment schedule and/or for one or more treatments, a modified amount, and/or a modified type, the one or more processors may submit for physician review the proposed modified treatment schedule or for one or more treatments, the proposed modified amount, and/or the proposed modified type.

The one or more processors may request the physician review as a healthcare service (64). The one or more processors may update the therapy information if the physician approves or corrects the modified treatment schedule and/or for one or more treatments, the modified treatment amount, and/or modified treatment type. In some examples, the one or more processors may initiate a healthcare service by submitting a query to physician device 36, causing that device to present the proposed modified treatment schedule, amount, and/or type to physician 34. After the review, physician 34 may return a physician response indicating either physician approval, rejection, or correction of the proposed modified treatment schedule, amount, and/or type. Regardless of which physician response is returned, the one or more processors may update the therapy information to indicate physician 34's approval, rejection, or correction of the proposed modified treatment schedule, amount, and/or type. In turn, the one or more processors may implement the modified or corrected treatment schedule, amount, and/or type, for example, by having the delivery device apply appropriate device settings.

The one or more processors may output data indicating completion of a healthcare service to a healthcare provider system (66). In some examples of the outputted data, updated therapy information may be part of an evidentiary submission for the healthcare service to a health care provider system (66). In some examples, the evidentiary submission may include data indicative of a completion of the physician review as the healthcare service or an event corresponding to patient 12. The one or more processors may generate an invoice requesting reimbursement for the healthcare service and automatically populate that invoice with correct data items, ensuring acceptance and approval by the health care provider system. On behalf of physician 34, the one or more processors may communicate a message with the invoice embedded within as part of the evidentiary submission. In this manner, the one or more processors may prevent or reduce a likelihood that the health care provider system rejects the invoice. In addition, because the one or more processors does not store any data if the invoice is rejected, the rejection of the invoice may result in missing data from patient 12's healthcare and medical records. Physician 34 benefits from the one or more processors automating reimbursement requests, for example, from spending little or no time handling reimbursement requires and having more time to handle other patients.

Figure 6A:
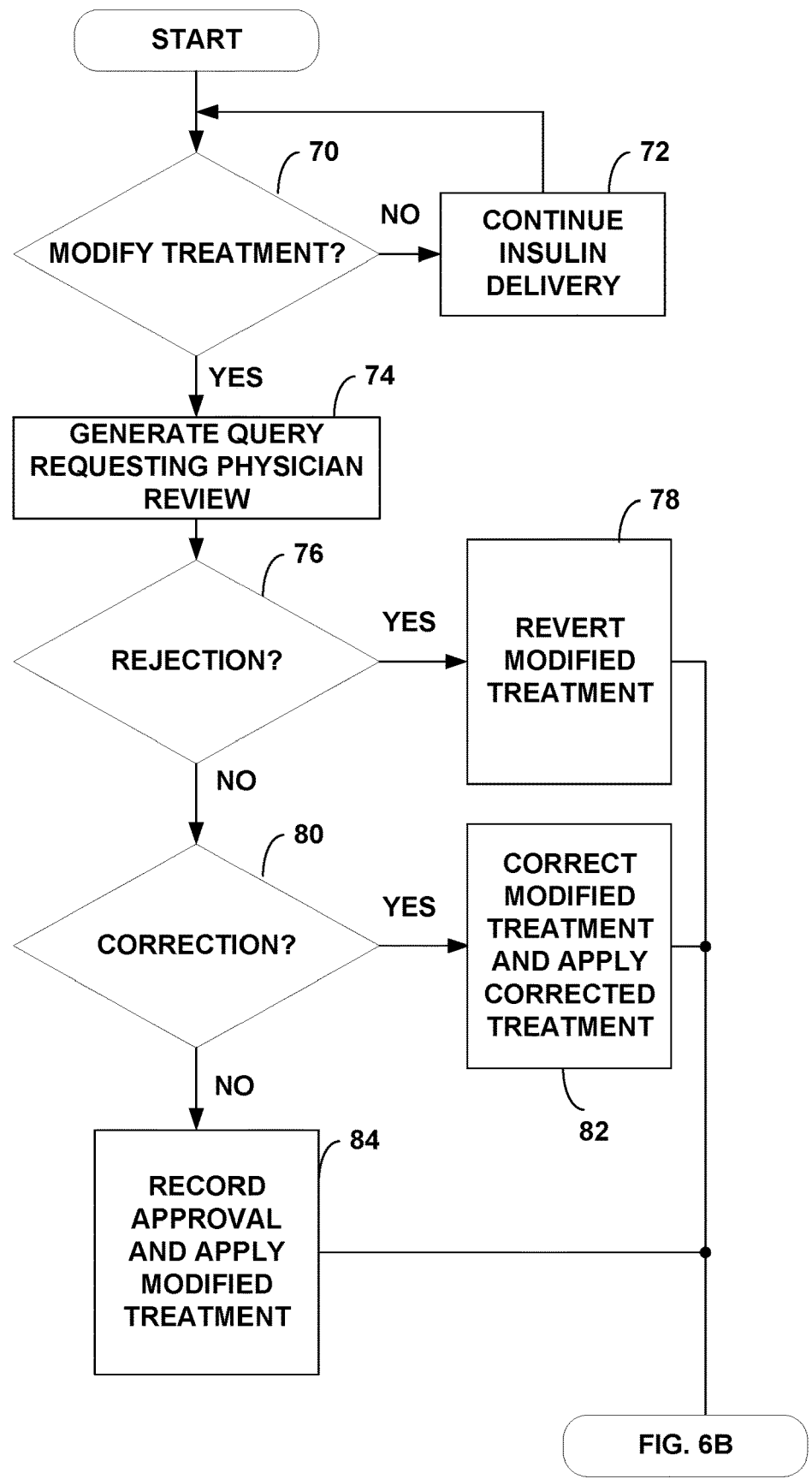
FIGS. 6A-6B are flow diagrams illustrating another example operation, in accordance with one or more examples described in this disclosure.
Figure 6B:
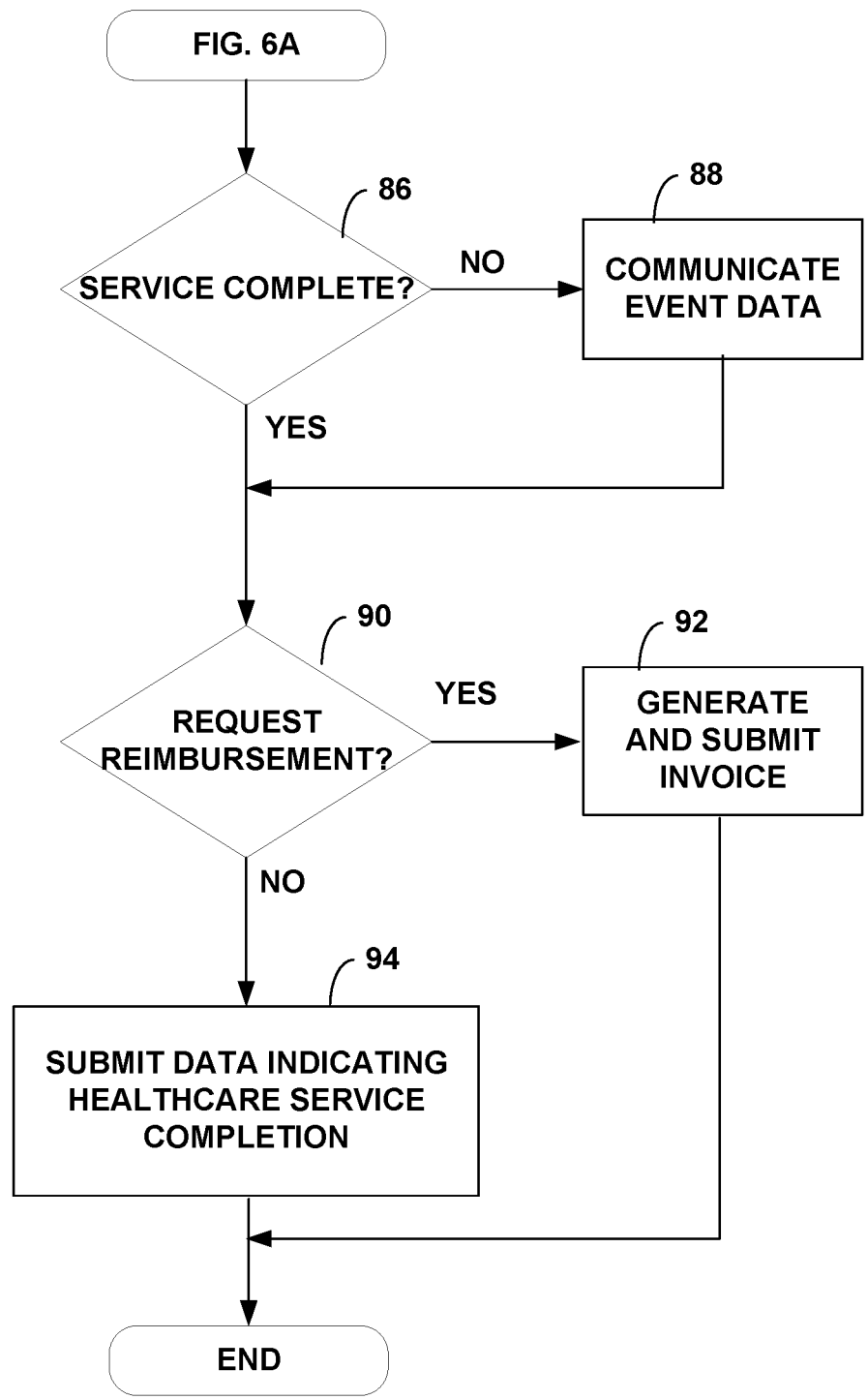

FIGS. 6A-6B are flow diagrams illustrating an example operation, in accordance with one or more examples described in this disclosure. The example operation may be performed on a patient (e.g., patient 12) using one or more of that patient's device(s), which includes one or more of wearable device 22, patient device 24, and/or cloud 26 as described in FIGS. 1-5. FIGS. 6A-6B are described with respect to one or more processors. The one or more processors may be one or more processors 28 of cloud 26, one or more processors of patient device 24 (e.g., processing circuitry 32), one or more processors of wearable device 22 (e.g., processing circuitry 40), one or more processors of insulin pump 14 (if available), one or more processors of injection device 30 (if available), or any combination thereof. While the patient may have access to any combination of wearable device 22, patient device 24, and/or cloud 26, FIGS. 6A-6B is described with respect to one or more processors generally.

As described herein, patient 12 and/or physician 34 may benefit from patient device 24, cloud 26, and/or physician device 36 performing the example operation, for example, by automating healthcare management operations. Automating reimbursement of legitimate healthcare services between patient 12 and/or physician 34 (or for only physician 34), one example healthcare management operation, may provide a number of benefits to patient 12 and/or physician 34. To physician 34's benefit, the one or more processors may handle submissions of reimbursement requests to healthcare provider 30, for example, by submitting the necessary information in an acceptable format for approval. The one or more processors may automatically submit a reimbursement request after determining satisfactory completion of physician 34's review of patient 12's current or proposed diabetes therapy. By doing so, the one or more processors facilitate a part of physician 34's business activity, providing physician 34 with income (e.g., additional income in some instances). Hence, the example operation depicted in FIGS. 6A-6B is an improvement over conventional healthcare management devices, systems, and techniques.

The example operation may commence by having the one or more processors determine whether to modify a treatment such as patient 12's current treatment for an unhealthy glucose level caused by diabetes (70). Based on determining not to modify a treatment (e.g., patient 12's current treatment) (NO of 70), the one or more processors may instruct a delivery device to continue delivering insulin according to the patient 12's current treatment (e.g., without modification) (72).

Based on determining to modify a treatment (e.g., patient 12's current treatment) (YES of 70), the one or more processors may generate a query requesting physician review of the modified treatment (74). When the one or more processors receive a physician response, the example operation may proceed by having the one or more processors determine whether the physician response indicates a rejection of the modified treatment (76). Based on determining that the physician response indicates a rejection of the modified treatment (YES of 76), the one or more processors may proceed to revert the modified treatment (e.g., forgo modifying patient 12's current treatment) (78). For example, the one or more processors may remove the modified treatment from the therapy information, allowing patient 12 to continue receiving diabetes therapy in accordance with a current treatment schedule.

Based on determining that the physician response does not indicate a rejection of the modified treatment (NO of 76), the one or more processors may proceed to determine whether the physician response indicates a correction of the modified treatment (80). Based on determining that the physician response indicates a correction of the modified treatment (YES of 80), the one or more processors may proceed to correct/revise the modified treatment in accordance with the physician response (82).

Based on determining that the physician response does not indicate a correction of the modified treatment (NO of 80), the one or more processors may proceed to record an approval by the physician and/or apply the modified treatment to patient 12 (84). In some examples, the one or more processors may communicate data describing the modified treatment to the delivery device and/or patient device 24 where each device or both devices may determine device settings and/or instructions for operating the delivery device to administer the modified treatment. In other examples, the one or more processors may translate the modified treatment (e.g., a modified treatment data/time, a modified treatment amount, and/or a modified treatment type) into compatible device settings and/or instructions that when applied (e.g., executed/implemented) by the delivery device, may result in the delivery device administering the modified treatment.

As further illustrated in FIG. 6A, the delivery device applies the current treatment, the modified treatment, or the corrected treatment based on the physician response. Turning to FIG. 6B, after the one or more processors applies an appropriate treatment schedule, amount, and type, the one or more processors may determine whether a healthcare service has been completed (86). If, following FIG. 6A, the one or more processors determine that the healthcare service has not been completed (NO of 86), the one or more processors may communicate event data corresponding to patient 12 (88). Circumstances may exist that prevent the healthcare service from being completed to satisfaction; as examples, patient 12 may have an interfering medical condition and/or the delivery device may have a malfunctioning component.

On the other hand, if the one or more processors determine that the healthcare service has been completed (YES of 86), the one or more processors may proceed to determine whether to automatically submit a reimbursement request for the completed healthcare service (e.g., without additional physician input) (90). In some examples, healthcare provider 30 (e.g., on behalf of patient 12) and physician 34 may have agreed to a reimbursement scheme for various healthcare services including services rendered through a cloud-based system such a remote monitoring/delivery service. One or more network devices in cloud 26 may run the remote monitoring/delivery service on behalf of another entity, such as the delivery device manufacturer (e.g., insulin pump manufacturer). As part of service's functionality, the remote monitoring/delivery service may operate a healthcare management data platform and a portal through which client applications running in physician devices and the data platform exchange data (e.g., queries for physician review and physician responses).

Based on determining that the physician should be reimbursed for the completed healthcare service (YES of 90), the one or more processors may automatically generate an invoice for the completed healthcare service and then, automatically submit that invoice to healthcare provider 30's system for reimbursement (e.g., without additional physician input) (92). The one or more processors may populate the invoice with approved identifiers and other data, ensuring that the invoice is accepted and the reimbursement is approved by the patient and/or the patient's insurance company. In some examples, one or more processors 28, physician device 36 and/or healthcare provider 30 may submit that invoice in a reimbursement request with the necessary evidence of a satisfactory completion of the healthcare service, and for at least that reason, the patient and/or the patient's insurance company accepts the request and approves the physician review as a reimbursable healthcare service.

To illustrate by way of example, the patient and/or the patient's insurance company may specify the following requirements for the patient's healthcare provider system to follow in order to receive reimbursement for the reimbursable healthcare service: 1) Qualified physician or health professional; 2) Documented consent in medical records; 3) If new patient or patient has not been seen within 1 year, a face to face visit is required; 4) 30 minutes of time per 30 days, billed once per patient; 5) Direct communication is not required; and 6) Remote Patient Monitoring (RPM) can be provided anywhere. The one or more processors may generate the invoice to include evidentiary information establishing that each requirement has been fulfilled. This may include the physician's name and physician's license number, patient name, timestamps, documents including signed documents by the patient and/or the physician, emails, medical records, and/or the like.

Based on determining that the physician cannot be reimbursed for the completed healthcare service (NO of 90), the one or more processors may proceed to automatically submit data indicating the completed healthcare service (e.g., without additional physician input) (94). Even if healthcare provider 30 does not consider the physician review as a reimbursable healthcare service, it still may be beneficial to submit data indicating the completed healthcare service or the event data corresponding to patient 12. If the one or more processors fail to submit such data or the submission is not accepted by healthcare provider 30's system, healthcare provider 30 may not record any descriptive information for the physician review or may record an insufficient amount information, resulting in missing data (e.g., important data) in patient 12's medical record. In a number of ways, patient 12 benefits from having a complete medical record. The example operation of FIGS. 6A-6B may guarantee healthcare provider 30 accepts the one or more processors' submission and records the description information for the physician review.

The example operation depicted in FIGS. 6A-6B, in general, includes the one or more processors submitting to healthcare provider 30 information describing one or more scheduled treatments (e.g., a next scheduled treatment). To illustrate by way of examples, the one or more processors may submit such information as evidence of satisfactory completion of a healthcare service. If patient 12 has a manual injection device (e.g., a syringe, insulin pen, and/or the like), the one or more processors may output data informing that patient of the next scheduled treatment (e.g., a next dosage) via a mobile device such as patient device 24, completing the physician review of patient 12's current therapy. As part of a data submission to healthcare provider 30, the one or more processors may output data of the next scheduled treatment in order to convey satisfactory completion of the physician review (e.g., as a healthcare service). If the patient has an insulin pen with a smart cap, a smart insulin pen, or a similar injection device, the one or more processors may output data indicating the next dosage to the smart cap, the smart insulin pen, or the similar injection device and, in turn, that injection device prepares or outputs information about the next dosage, also completing the physician review. Similar to the manual injection device, the one or more processors may output data of the next dosage as part of a data submission to healthcare provider 30. If patient 12 has an insulin delivery device such as an example of insulin pump 14, the one or more processors may output data describing the next dosage to the insulin delivery device, which may automatically administer the next dosage to patient 12. Similar to the manual injection device, the insulin pen with a smart cap, or the smart insulin pen, the one or more processors may submit data describing the next dosage as to healthcare provider 30.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable device 22, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A system for therapy delivery, the system comprising:
a delivery device configured to execute therapy information for directing the therapy delivery for a patient, wherein the therapy information comprises a treatment schedule specifying one or more treatments over a time period, wherein for each of the one or more treatments, the therapy information comprises a treatment type and a treatment amount; and
processing circuitry communicably coupled to the delivery device, the processing circuitry configured to:
determine a modification to the therapy information based on a recommendation of a digital twin, wherein the digital twin determines an estimated glucose level expected to be within a healthy range if the delivery device executes the modification to therapy information; and
in response to physician review of the modification to the therapy information, output, to a healthcare provider system for the patient, data indicating completion of a healthcare service corresponding to the physician review.

2. The system of claim 1, further comprising a physician device configured to present a query requesting the physician review of at least one of a modified treatment schedule, a modified treatment type, or a modified treatment amount.

3. The system of claim 2, wherein to output the data indicating completion of a healthcare service, the processing circuitry is further configured to: in response to a physician rejection of the at least one of the modified treatment schedule, the modified treatment type, or the modified treatment amount, revert the at least one of the modified treatment schedule, the modified treatment type, or the modified treatment amount.

4. The system of claim 2, wherein to output the data indicating completion of a healthcare service, the processing circuitry is further configured to: in response to a physician correction of the at least one of the modified treatment schedule, the modified treatment type, or the modified treatment amount, correct the at least one of the modified treatment schedule, the modified treatment type, or the modified treatment amount in accordance with the physician correction.

5. The system of claim 2, wherein to output the data indicating completion of a healthcare service, the processing circuitry is further configured to: in response to a physician approval of the at least one of the modified treatment schedule, the modified treatment type, or the modified treatment amount, update the therapy information to include the at least one of the modified treatment schedule, the modified treatment type, or the modified treatment amount.

6. The system of claim 5, wherein to output the data indicating completion of a healthcare service, the processing circuitry is further configured to output at least one of device settings or instructions to the delivery device for executing the updated therapy information, wherein the delivery device is to administer a treatment to the patient in accordance with the at least one of the modified treatment schedule, the modified treatment type, or the modified treatment amount.

7. The system of claim 1, wherein to output the data indicating completion of a healthcare service, the processing circuitry is further configured to: populate form data with identifying information for the healthcare service.

8. The system of claim 1, wherein to output the data indicating completion of a healthcare service, the processing circuitry is further configured to output an invoice for the healthcare service.

9. The system of claim 1, wherein to output the data indicating completion of a healthcare service, the processing circuitry is further configured to:
update the estimated glucose level based on glucose level readings captured by the delivery device; and
calibrate delivery device settings to achieve a healthy patient glucose level.

10. A device for therapy delivery, the device comprising:
processing circuitry communicably coupled to a delivery device for executing therapy information configured to direct the therapy delivery for a patient, wherein the therapy information comprises a treatment schedule specifying at least one treatment over a time period, wherein for each of the at least one treatment, the therapy information comprises a treatment schedule, a treatment type and a treatment amount, the processing circuitry configured to:

determine a modification to the therapy information based on a recommendation from a digital twin, wherein the digital twin determines an estimated glucose level expected to be within a healthy range if the delivery device executes the modification to the therapy information; and in response to a physician review of the modification to the therapy information, output, to a healthcare provider system for the patient, data indicating completion of a healthcare service corresponding to the physician review.

11. The device of claim 10, wherein to output the data indicating completion of the healthcare service, the processing circuitry is further configured to generate a query for presentation on a physician device, the query comprising the estimated glucose level and a request for a physician rejection, a physician approval, or a physician correction of at least one of a modified treatment schedule, a modified treatment type, or a modified treatment amount.

12. The device of claim 11, wherein to update the therapy information, the processing circuitry is further configured to: in response to the physician review of the at least one of the modified treatment schedule, the modified treatment type, or the modified treatment amount, update the therapy information to perform at least one of:

reverting the at least one of a modified treatment schedule, a modified treatment type, or a modified treatment amount based on the physician review;

storing the at least one of a modified treatment schedule, a modified treatment type, or a modified treatment amount based on the physician review; and correcting the at least one of a modified treatment schedule, a modified treatment type, or a modified treatment amount based on the physician review.

13. The system of claim 12, wherein to output the data indicating completion of the healthcare service, the processing circuitry is further configured to revert the at least one of a modified treatment schedule, a modified treatment type, or a modified treatment amount back to at least one of a default treatment schedule, a default treatment type, or a default treatment amount.

14. The system of claim 12, wherein to output the data indicating completion of the healthcare service, the processing circuitry is further configured to revert the at least one of a modified treatment schedule, a modified treatment type, or a modified treatment amount back to at least one of the treatment schedule, the treatment type, or the treatment amount.

15. The device of claim 14, wherein to output the data indicating completion of the healthcare service, the processing circuitry is further configured to output the updated therapy information in an invoice requesting reimbursement for the healthcare service.

16. A method for therapy delivery, the method comprising:

executing, by a delivery device, therapy information configured to direct the therapy delivery for a patient, wherein the therapy information comprises a treatment schedule specifying at least one treatment over a time period, wherein for each of the at least one treatment, the therapy information comprises a treatment schedule, a treatment type and a treatment amount;

determine a modification to the therapy information based on a recommendation from a digital twin, wherein the digital twin determines an estimated glucose level expected to be within a healthy range if the delivery device executes the modification to the therapy information; and in response to physician review of the modification to the therapy information, outputting, to a healthcare provider system for the patient, data indicating completion of a healthcare service corresponding to the physician review.

17. The method of claim 16, wherein outputting the data indicating completion of the healthcare service further comprises outputting an invoice requesting reimbursement for the completion of the healthcare service.

18. The method of claim 16, wherein outputting the data indicating completion of the healthcare service further comprises outputting at least one of device settings or instructions to the delivery device for execution, the delivery device is to administer a treatment to the patient in accordance with at least one of a modified treatment schedule, a modified treatment type, or a modified treatment amount.

19. The method of claim 16, wherein outputting the data indicating completion of the healthcare service further comprises generating a query for presentation on a physician device, the query comprising the estimated glucose level and a request for a physician rejection, a physician approval, or a physician correction of at least one of modified treatment schedule, modified treatment type, or modified treatment amount.

20. The method of claim 19, wherein outputting the data indicating completion of the healthcare service further comprises: in response to the physician review of the at least one of a modified treatment schedule, the modified treatment type, or the modified treatment amount, performing at least one of:

reverting the at least one of the modified treatment schedule, the modified treatment type, or the modified treatment amount based on the physician review;

storing the at least one of the modified treatment schedule, the modified treatment type, or the modified treatment amount based on the physician review; or correcting the at least one of the modified treatment schedule, the modified treatment type, or the modified treatment amount based on the physician review.

* * * * *